US009668474B2

(12) United States Patent
Hawkins et al.

(10) Patent No.: US 9,668,474 B2
(45) Date of Patent: Jun. 6, 2017

(54) STRUCTURED SURFACTANT SUSPENDING SYSTEMS

(71) Applicant: Stepan Company, Northfield, IL (US)

(72) Inventors: John Hawkins, Grenoble (FR); Emilie Pace, Grenoble (FR); Laetitia Lebert, La Tronche (FR)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 14/455,035

(22) Filed: Aug. 8, 2014

(65) Prior Publication Data

US 2014/0348759 A1 Nov. 27, 2014

Related U.S. Application Data

(63) Continuation of application No. PCT/US2013/025282, filed on Feb. 8, 2013.

(30) Foreign Application Priority Data

Feb. 10, 2012 (GB) .................................... 1202333.9

(51) Int. Cl.

| A61K 8/04 | (2006.01) |
|---|---|
| A01N 25/30 | (2006.01) |
| C11D 17/00 | (2006.01) |
| A61Q 5/02 | (2006.01) |
| A61Q 19/10 | (2006.01) |
| A61K 8/34 | (2006.01) |
| A61K 8/37 | (2006.01) |
| A61K 8/41 | (2006.01) |
| A61K 8/44 | (2006.01) |
| A61K 8/46 | (2006.01) |
| A61K 8/60 | (2006.01) |
| A61K 8/86 | (2006.01) |
| A61K 8/14 | (2006.01) |
| C11D 1/14 | (2006.01) |
| C11D 1/29 | (2006.01) |
| C11D 1/66 | (2006.01) |
| C11D 1/72 | (2006.01) |
| C11D 1/75 | (2006.01) |
| C11D 1/90 | (2006.01) |
| C11D 1/92 | (2006.01) |

(52) U.S. Cl.
CPC ............... *A01N 25/30* (2013.01); *A61K 8/14* (2013.01); *A61K 8/342* (2013.01); *A61K 8/375* (2013.01); *A61K 8/41* (2013.01); *A61K 8/44* (2013.01); *A61K 8/442* (2013.01); *A61K 8/463* (2013.01); *A61K 8/60* (2013.01); *A61K 8/86* (2013.01); *A61Q 5/02* (2013.01); *A61Q 19/10* (2013.01); *C11D 1/667* (2013.01); *C11D 17/0026* (2013.01); *A61K 2201/012* (2013.01); A61K 2201/24 (2013.01); A61K 2800/262 (2013.01); A61K 2800/30 (2013.01); A61K 2800/596 (2013.01); C11D 1/146 (2013.01); C11D 1/29 (2013.01); C11D 1/662 (2013.01); C11D 1/72 (2013.01); C11D 1/75 (2013.01); C11D 1/90 (2013.01); C11D 1/92 (2013.01)

(58) Field of Classification Search
CPC ........................................................ A61K 8/06
See application file for complete search history.

(56) References Cited

U.S. PATENT DOCUMENTS

| 5,443,840 | A | 8/1995 | Morancais et al. |
|---|---|---|---|
| 5,478,490 | A | 12/1995 | Russo et al. |
| 5,707,648 | A * | 1/1998 | Yiv ..................... A61K 9/1075 264/4.1 |
| 5,783,200 | A | 7/1998 | Motley et al. |
| 5,866,110 | A | 2/1999 | Moore et al. |
| 5,945,092 | A | 8/1999 | Krog et al. |
| 5,964,692 | A | 10/1999 | Blezard et al. |
| 6,033,710 | A | 3/2000 | Miller et al. |
| 6,277,404 | B1 | 8/2001 | Laversanne et al. |
| 6,383,471 | B1 * | 5/2002 | Chen et al. ..................... 424/45 |
| 7,696,254 | B2 | 4/2010 | Suzuki et al. |
| 8,148,308 | B2 | 4/2012 | Ryklin et al. |
| 2004/0002438 | A1 | 1/2004 | Hawkins et al. |
| 2004/0081633 | A1 | 4/2004 | Mercier et al. |
| 2004/0235702 | A1 | 11/2004 | Hawkins |
| 2006/0178441 | A1 * | 8/2006 | Hawkins ......................... 516/77 |
| 2007/0087104 | A1 | 4/2007 | Chanamai |
| 2009/0197785 | A1 | 8/2009 | Hawkins |
| 2009/0291056 | A1 | 11/2009 | Castro et al. |
| 2011/0117019 | A1 | 5/2011 | Hawkins |
| 2011/0223125 | A1 | 9/2011 | Hough et al. |

FOREIGN PATENT DOCUMENTS

| CA | 2 168 260 | 4/2000 |
|---|---|---|
| EP | 0 086 614 | 8/1983 |
| EP | 0 452 106 | 4/1991 |
| EP | 0 530 708 | 8/1992 |
| EP | 0820755 A2 | 1/1998 |

(Continued)

OTHER PUBLICATIONS

International Search Report and Written Opinion dated Apr. 17, 2013 for PCT Application No. PCT/US2013/025282 filed Feb. 8, 2013.

(Continued)

*Primary Examiner* — Frederick Krass
*Assistant Examiner* — Amanda Heyes
(74) *Attorney, Agent, or Firm* — McAndrewss, Held & Malloy, Ltd.

(57) ABSTRACT

A structured surfactant system with a very high degree of clarity. The system comprises water and a mixture of at least one surfactant having a HLB (Hydrophilic Lipophilic Balance) value of less than 10, and at least one surfactant having an HLB value of 10 or greater. The structured surfactant system forms multilamellar vesicles and has suspending properties without added electrolytes, carbohydrates, or polymeric thickeners. This makes the structured surfactant system particularly useful in personal care compositions.

16 Claims, 1 Drawing Sheet

(56) References Cited

FOREIGN PATENT DOCUMENTS

| EP | 2492333 | 8/2012 |
|---|---|---|
| GB | 2464393 A | 4/2010 |
| JP | H04224507 | 8/1992 |
| JP | H04264015 | 9/1992 |
| JP | H06219923 | 8/1994 |
| JP | 2001270807 | 10/2001 |
| JP | 2001288036 | 10/2001 |
| JP | 2004002292 | 1/2004 |
| JP | 2006022061 | 1/2006 |
| WO | 00/36079 | 6/2000 |
| WO | 01/00780 | 1/2001 |
| WO | 01/34111 | 5/2001 |
| WO | 01/56534 | 9/2001 |
| WO | 2005/053612 A2 | 6/2005 |
| WO | 2005/092370 | 10/2005 |
| WO | 2008/071965 | 6/2008 |
| WO | 2009/034360 | 3/2009 |
| WO | 2009/098469 A1 | 8/2009 |
| WO | 2010/054495 | 5/2010 |
| WO | 2010/054495 A2 | 5/2010 |

OTHER PUBLICATIONS

European Patent Office, Communication with extended European search report in Application No. 13746918.5 dated Jul. 16, 2015 (9 pages).
Bendejacq Denis et al: "Structured Surfactant Systems for High Performance Shampoos", Cosmetics & Toiletries, Wheaton, IL, US, vol. 125, No. 11, Nov. 1, 2010 (Nov. 1, 2010), pp. 22-29, XP008176922, ISSN: 0361-4387.

* cited by examiner

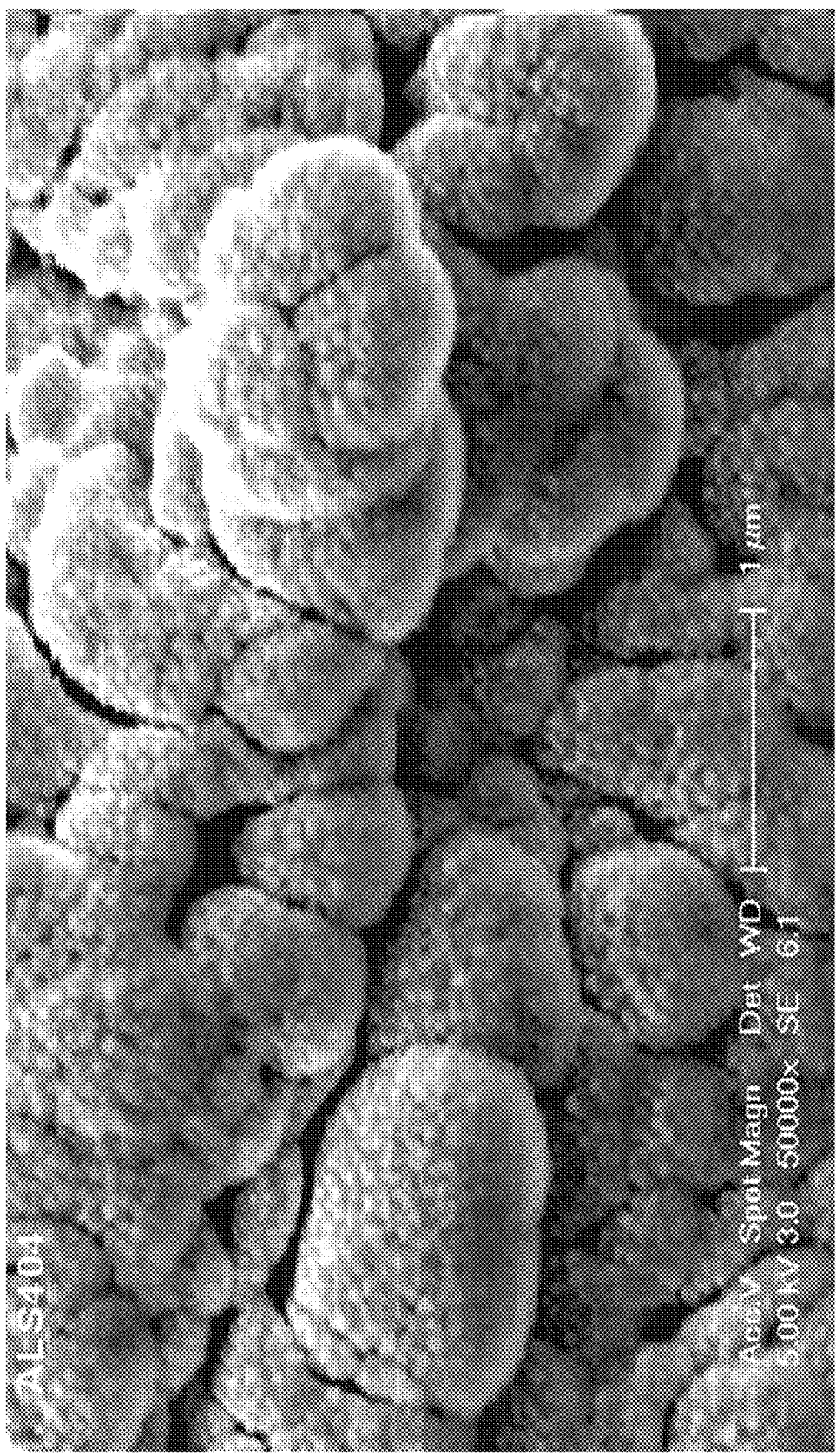

STRUCTURED SURFACTANT SUSPENDING SYSTEMS

FIELD OF THE INVENTION

The present technology relates to structured surfactant suspending systems and compositions containing the structured surfactant suspending systems, particularly personal care compositions.

BACKGROUND OF THE INVENTION

Formulating suspensions of water insoluble, or sparingly soluble solids and/or liquids in personal care compositions such as shampoos and body washes presents a long-standing problem. Formulators need to be able to suspend a variety of such ingredients. For example oils, anti-dandruff agents, such as zinc pyrithione, hair conditioners including cationic polymers, and opacifiers such as mica are widely used. There is therefore a need to disperse/suspend them in aqueous shampoos and body washes.

We have discovered novel structured surfactant systems that are capable of suspending solid particles and oils without sedimentation, using high foaming surfactant systems which give dense stable foams and good skin feel.

The term "structured system" as used herein means a pourable composition comprising water, surfactant, and optionally other dissolved matter, which together form a mesophase, or a dispersion of a mesophase in a continuous aqueous medium, and which has the ability to immobilize non-colloidal, water-insoluble particles, while the system is at rest, thereby forming a stable, pourable suspension. Surfactants and water interact to form phases that are neither liquids nor crystals; these are usually termed "liquid crystal phases," or alternatively "mesomorphic phases" or "mesophases."

The term "pourable" is used herein to refer to shear thinning fluids having viscosities around 2000 cps (Brookfield RVT viscometer, spindle 5, speed 100) at room temperature.

Attempts to solve the problem of dispersing water insoluble materials in water have generally involved either using gums or other polymeric thickeners to raise the viscosity of the liquid medium, or else forming colloidal dispersions. More recently the use of lamellar structured surfactants has been proposed.

Gums and polymeric thickeners, which increase the viscosity of the liquid medium, retard, but do not prevent sedimentation, and at the same time make the composition harder to pour. They do not provide stable suspensions.

Colloidal dispersions are prevented from sedimenting by Brownian motion. Such systems are usually incapable of dispersing relatively coarse particles.

Lamellar structured suspending systems depend on the rheological properties of the suspending medium to immobilize the particles, rather than size of the particles. This requires the suspending medium to exhibit a significant yield point that can counteract the sedimenting or creaming of the suspended particles, but is low enough to enable the medium to flow under externally imposed stresses, such as pouring and stirring, like a normal liquid. The structure reforms sufficiently rapidly to prevent sedimentation, once the agitation caused by the external stress has ceased.

Lamellar structured systems all involve the L[alpha]-phase, in which bilayers of surfactant are arranged with the hydrophobic part of the molecule on the interior and the hydrophilic part on the exterior of the bilayer (or vice versa). The bilayers lie side by side, e.g. in a parallel or concentric configuration, sometimes separated by aqueous layers. L[alpha]-phases (also known as G-phases) can usually be identified by their characteristic textures under the polarizing microscope and/or by x-ray diffraction, which is often able to detect evidence of lamellar symmetry. Such evidence may comprise first, second and sometimes third order peaks with a d-spacing (2[pi]/Q, where Q is the momentum transfer vector) in a simple integral ratio 1:2:3. Other types of symmetry give non-integral ratios. The d-spacing of the first peak in the series corresponds to the repeat spacing of the bilayer system.

Most surfactants form an L[alpha]-phase either at ambient or at some higher temperature when mixed with water in certain specific proportions. However, these conventional L[alpha]-phases do not function as structured suspending systems. Useful quantities of solid render them unpourable, and smaller amounts tend to sediment.

The main type of structured system used in practice is based on dispersed spherulitic phase. Spherulitic phases comprise well-defined spheroidal bodies, usually referred to in the art as spherulites, in which surfactant bilayers are arranged as concentric shells. The spherulites usually have a diameter in the range 1000 to 15000 angstroms and are dispersed in an aqueous phase in the manner of a classical emulsion. Spherulitic systems are described in more detail in EP 0 151 884.

Most lamellar structured surfactants require the presence of a structurant, as well as surfactant and water in order to form structured systems capable of suspending solids. The term "structurant" is used herein to describe any non-surfactant, capable, when dissolved in water, of interacting with surfactant to form or enhance (e.g. increase the yield point of) a structured system. It is typically a surfactant-desolubiliser, e.g. an electrolyte. However, certain relatively hydrophobic surfactants such as isopropylamine alkyl benzene sulphonate can form spherulites in water in the absence of electrolyte. Such surfactants are capable of suspending solids in the absence of any structurant, as described in EP 0 414 549.

A major problem with lamellar suspending systems, from the point of view of the formulator of personal care products, is that they are formed most readily by surfactant systems that operate as detergents. The higher foaming surfactants (which are most effective in personal care products, such as shampoos) are more soluble in water and are classed as solubilizers.

Attempts to form stable lamellar suspending systems with high foaming surfactant systems have entailed the use of high concentrations of surfactant and high levels of structurant, such as electrolyte or sugar.

In general the use of high surfactant levels, e.g. greater than about 15-20% by weight, is undesirable on grounds both of cost and the potential for producing adverse effects on skin or hair. High electrolyte levels are similarly undesirable, for their potential effects on skin and hair.

Spherulitic surfactant systems induced with high levels of electrolytes are opaque and this limits the visual effects that can be achieved and may be perceived as less attractive than a clear system in some applications. This is because light cannot pass through the dense matrix of spherulites. By contrast many liquids and gases are transparent because light can pass more readily between the large spaces between their atoms. Many crystals are both solid and transparent, this is because the atoms of a crystal are arranged in a precise lattice structure, stacked in regular rows, with regular spacing between them and hence there are many pathways that a light beam can take through a crystal lattice. Solids can also become transparent if their atoms are arranged randomly, glass and sugar candy are good examples.

Transparency can be obtained in certain spherulitic surfactant systems by adding high levels of soluble carbohydrate (e.g. sucrose); but the sugar generally needs to be present in undesirably high concentrations, e.g. over 20% to be effective. Such systems are described in more detail in US2004235702.

There is therefore a need, especially in the personal care field, for a suspending system that contains a blend of high foaming surfactants and is transparent and mobile; but which does not require the presence of electrolyte or sugar as a structurant.

BRIEF SUMMARY OF THE INVENTION

It has surprisingly been found that transparent structured surfactant suspending systems can be formed by mixing a particular selection of surfactants in particular amounts in the substantial absence of electrolytes or carbohydrates. The transparent structured surfactant systems are particularly useful in personal care compositions to achieve a variety of aesthetically pleasing visual effects. The surfactant systems are mobile, have good suspending power and are phase stable.

In a first aspect, the present technology provides a transparent structured surfactant system which is comprised of multilamellar vesicles with a bilayer spacing below 60 angstroms.

In another aspect, the present technology provides an aqueous structured surfactant system comprising water and a mixture of surfactants, wherein the mixture of surfactants, comprises at least one surfactant having an HLB value of less than 10, alternatively less than 8; and at least one surfactant having an HLB value of 10 or greater, the mixture of surfactants having an overall HLB value in the range of about 11 to about 13; wherein the structured surfactant system is free of electrolytes and polymeric thickeners; and wherein the structured surfactant system is substantially transparent in the absence of any suspended matter and has suspending properties.

BRIEF DESCRIPTION OF SEVERAL VIEWS OF THE DRAWINGS

FIG. 1 is an electron micrograph illustrating microvesicles of the structured surfactant system.

DETAILED DESCRIPTION OF THE INVENTION

The present technology relates to a structured suspending system that is based on a lamellar surfactant mesophase. It is transparent, high foaming, can be very low in electrolyte, and can be made without sugar, which makes it ideal for personal care applications. The structured surfactant system comprises water and a mixture of surfactants that form transparent structured liquid compositions in the absence of added electrolytes or carbohydrates. As used herein, the term "transparent" means having the property of transmitting rays of light through its substance so that bodies situated beyond or behind can be distinctly seen. The transparency of the compositions does not preclude the compositions from being colored, for example by the addition of a dye, provided the dye does not detract from the substantial transparency of the composition. Further, the transparency of the compositions does not preclude the compositions from containing various particles to achieve a variety of different effects. For example, mica particles could be suspended in the composition to provide visually pleasing effects, if desired, which would reduce the transparency of the composition. In that case the definition of transparency is applied to the structured liquid composition without the addition of any suspended matter. Transparency can also be measured by methods known in the art. For example, a spectrophotometer can be used to measure the absorption of visible light between 380 and 800 nm. In some embodiments of the present structured surfactant systems, transmission is greater than 50%, more typically greater than 60%.

Analysis of the structured suspending systems (with small angle X-ray, scanning electron microscopy, and rheology) suggests that the majority of the structure units comprise multilamellar microvesicles (i.e. very small spherulites) with around 5-7 concentric shells, alternatively 4-7 concentric shells, and a bi-layer separation of about 45 angstroms. FIG. 1 is an electron micrograph showing the microvesicles of the structured surfactant system. The microvesicles are the submicron objects seen on the surface of the large clumps depicted in FIG. 1. From the electron micrograph, it is estimated that the microvesicles have a diameter of about 300 to about 1000 Angstroms. It is believed that the microvesicles or spherulites are arranged in a precise lattice structure stacked in regular rows, with regular spacing, and this is one possible reason why the compositions have a high degree of transparency and optical clarity. In addition, because the greater proportion of the surfactants that are used contain a terminal hydroxyl group, the spherulites have a refractive index that is close to water. This means that they transmit rather than scatter light, and the refractive index of the continuous medium can be easily matched to give complete transparency by the addition of small amounts of glycerol (for example). This particular structure has hitherto not been identified in the art as a suspending system. Surfactant HLB, headgroup, and shape are all important factors in determining whether a particular blend of surfactants will form this structure. For example, it has been found that the low HLB surfactant must be essentially linear and not possess a bulky hydrophilic headgroup. It may also be important that the low HLB surfactant have a saturated alkyl chain, and possess at least one terminal hydroxyl group.

In so far that it is practicable, it has not been found to be necessary to formulate these systems with any appreciable quantities of electrolyte. It is believed that without electrolyte, the spherulites are dispersed in water and pushed apart into a precise lattice by the electrical charge on the surface of the spherulites (in the case of non-ionic surfactant the charge will be induced by the polarized headgroup). When electrolyte is present it shields the surface charge and allows the spherulites to approach and 'jostle' each other.

The surfactants for use in preparing the structured surfactant system comprise a mixture of at least one surfactant having a hydrophilic-lipophilic balance (HLB) value that is low, for example less than 10, and at least one surfactant having a high HLB value, for example 10 or greater. Typically, the high HLB value will not exceed 40. Surfactants having a low HLB value are lipophilic and have low solubility in water. Surfactants having a high HLB value are hydrophilic and have a high solubility in water. The combination of surfactants together should have an HLB value of about 11 to about 13, preferably about 12.

The surfactants should be present in a concentration of at least 5% by weight of the structured surfactant system. Useful surfactant concentrations range from about 5% to about 40% by weight, alternatively about 5% to about 30% by weight of the structured surfactant system and include any percentage or range there between. Preferred total concentrations of the surfactants range from about 7% to about 20% alternatively about 10% to about 15%.

The low HLB surfactant has an HLB value of less than 10, alternatively less than 9, alternatively less than 8, alternatively less than 7, alternatively less than 6, alternatively less than 5. Particularly useful surfactants having a low HLB value are glyceryl fatty acid esters. Such glyceryl fatty acid esters are made by esterifying glycerin with medium to long chain fatty acids having from 6 to about 18 carbon atoms. The resulting product comprises a mixture of mono-, di-, and/or triglycerides of fatty acids, the relative proportions depending on the process used and the ratio of reactant employed. Preferred glyceryl fatty acid esters are mixtures of mono- and di-glycerides of caprylic and capric acids. A commercially available example of glyceryl caprylate/caprate can be obtained from Stepan Company, Northfield, Ill., under the tradename Stepan-Mild® GCC. The HLB value of Stepan-Mild® GCC is in the range of about 5 to about 6. Other useful low HLB surfactants include fatty alcohol ethoxylates with about 1 to 4, alternatively 2 to 3 moles of ethylene oxide, fatty alcohols, such as, for example, cetyl alcohol, and fatty acids, such as, for example, lauric, stearic, or palmitic acids. Mixtures of the low HLB surfactants can also be utilized. For example, fatty alcohols at levels of about 1% by weight in combination with glycerol esters provide a foam boosting/enhancing effect.

The high HLB surfactant has an HLB value of 10 or greater and can be an anionic, cationic, nonionic or amphoteric surfactant. Suitable anionic surfactants include soaps, sulfonated alkyl benzene, sulfonated methyl esters, sulfonated alpha olefin, paraffin sulfonate, alkyl alkoxy carboxylate, alkyl phosphate, alkyl alkoxy phosphate, alkyl sulfate, alkyl alkoxy sulfate, taurides, acyl lactylate, alkyl isethionate, acyl sarcosinate, sulfosuccinates, glutamates, and combinations thereof.

Suitable cationic surfactants include alkyl dimethyl ammonium halogenide, esterquat, amidoquat, and stearamidopropyl dimethyl amine quat. Suitable nonionic surfactants include alkylpolyglucosides, ethoxylated fatty alcohols, ethoxylated sorbitan esters, ethoxylated fatty acid alkanolamides, ethoxylated fatty amines, and sucrose esters.

Suitable amphoteric surfactants include betaines, sulfobetaines, propionates, glycinates, and amphoacetates. The high HLB surfactant can also be amine oxide or alkylated amine oxide preferably having a carbon chain length in the range of about 10-18 carbons. Mixtures of high HLB surfactants may also be employed. Preferred high HLB surfactants are those that contain no or minimal levels of electrolyte. Alkyl sulfates, alkyl ether sulfates and sarcosinates are particularly suitable high HLB surfactants.

The low and high HLB surfactants are mixed together in relative proportions in order to obtain a resulting HLB of the mixture in the range of about 11 to about 13, preferably about 12. In general, the ratio of the low HLB surfactant to high HLB surfactant in the surfactant system can range from about 4:1 to about 1:4, depending upon the particular surfactants selected.

The structured surfactant system can further include a component to adjust the refractive index to improve the optical clarity of the system. Without being bound by theory, it is believed that when appropriate ratios of the low HLB surfactant and the high HLB surfactant are mixed together, the mixture of surfactants forms liquid crystal dispersions composed of spherulites arranged in a precise lattice structure in the dispersing medium, for example water. Adding a component to the structured surfactant system to adjust the refractive index of the continuous, dispersing medium so that it is closer to that of the spherulites, results in improved optical clarity of the structured surfactant system.

Suitable materials for adjusting the refractive index include polyhydroxy compounds having at least two hydroxyl groups, such as, for example, ethylene glycol, propylene glycol, butylene glycol, glycereth-7, glycerol, polyglycerol, trimethylolpropane, pentaerythritol, and sorbitol. Glycerol is a preferred material and mixtures of glycerol and polyglycerol (e.g. triglycerol) are also preferred. It is believed that as well as altering the refractive index, polyglycerols also improve clarity by promoting the formation of small spherulites. Mixtures of glycerol and polyglycerols show synergism since they are around twice as effective at clarifying compositions as either glycerol or polyglycerol alone. The amount of material added will depend upon how much adjustment is needed. In general, the amount of hydroxyl-containing material added will range from about 1% to about 15% by weight, alternatively, about 1% to about 10% by weight of the structured surfactant system. More usually the amount will be between about 2% to about 6% by weight of the structured surfactant system. Blends of 50% glycerol plus 50% polyglycerol (e.g. triglycerol) have been found to be particularly effective.

It has further been discovered that clarity may be enhanced by incorporating a proportion of polyoxyethylene groups. These have been found to function when they are present as simple polyoxyethylene chains, i.e. polyethylene glycols; and also when they comprise the hydrophilic component of a surfactant, e.g. ethoxylated sorbitan ester. For example, in some embodiments, amounts of 0.5% PEG (as PEG 400) and 1% of POE (20) sorbitan monolaurate have been found to be effective.

The structured surfactant system of the present technology has good yield value. By "yield value" is meant that the structured surfactant system has the ability to support particulate (gas, solid, liquid) matter. The yield value enables the structured surfactant system to suspend solid, liquid or gas particles throughout a liquid composition.

The composition may contain suspended solid, liquid or gaseous particles. For instance the composition may contain suspended oil droplets. The oil is preferably a mineral oil (e.g. a low molecular weight petroleum oil) or a fatty glyceride or other ester such as lauryl acetate, a terpene oil such as limonene or a silicone oil. Mixtures of oils may be used. Particularly preferred are vegetable oils such as coconut, evening primrose, groundnut, meadow foam, apricot kernel, peach kernel, avocado, jojoba and olive oil. Oil soluble cosmetic or topical pharmaceutical ingredients may be dissolved in the oil including antiseptics, styptics, anti-dandruff agents such as zinc omadine (zinc pyrithione) and selenium disulphide, proteins, emollients such as lanolin, isopropyl myristate, glyceryl isostearate or propylene glycol distearate, dyes, perfumes and waxes. Water insoluble particulate solids may be suspended including exfoliants such as talc, clays, polymer beads, sawdust, silica, seeds, ground nutshells and dicalcium phosphate, pearlizers such as mica or glycerol or ethylene glycol di-stearate, glitter additives and sunscreens such as titanium dioxide and zinc oxide. Porous particles (so called micro-sponges) containing absorbed active ingredients or gelatin or other microcapsules may also be suspended. Other active ingredients which may be suspended include insect repellents and topical pharmaceutical preparations, e.g. preparations for treatment of acne, fungicides for athlete's foot or ringworm or antiseptics or antihistamines. Pigments, such as the iron oxides, may also be added. The particle size of the suspended material can vary widely, for example from about 5 microns to several millimeters in size.

The suspended particles can be added to personal care compositions for purely aesthetic reasons to achieve visually pleasing effects. Alternatively, the structured surfactant systems can be used in other applications where water insoluble or sparingly soluble components are utilized, such as in laundry and fabric softener compositions, agricultural compositions containing pesticides and insecticides, pharmaceutical suspensions, and hard surface cleaners containing abrasives, for example calcium carbonate.

The structured surfactant systems can be prepared by mixing the components at room temperature, then storing overnight at a temperature of about 55° C., alternatively about 45° C. The components are then remixed and cooled to room temperature. When mixing the compositions it is important to sequence the order of mixing to avoid the formation of liquid/liquid emulsions. These will tend to form if the oil soluble surfactants are added to a stirred solution of the high HLB surfactants. Liquid/liquid emulsions are metastable suspensions of liquid droplets, whereas the structured surfactant systems described herein are typically stable dispersions of liquid crystals. To avoid forming liquid/liquid emulsions it is preferred that all the surfactants are blended together to give a high active concentrate before they are added to the water. The high active concentrates have been found to be pourable and to disperse readily with low shear mixing at room temperature to form the structured surfactant. The resulting structured surfactant systems are transparent, and flowable, and achieve good suspending ability without the addition of electrolytes, carbohydrates or polymeric thickeners. They can be used alone as a liquid cleansing composition, for example as a body wash, hand wash, shampoo or the like. Alternatively, other optional ingredients may be added to make the structured surfactant systems suitable for a variety of different uses, such as a water-based scrub, a textile wash/softener and the like.

Optional ingredients include fatty acid soaps, builders, and additional surfactants to aid in cleaning ability. Emollients (including, without limitation, vegetable oils, mineral oils, silicone oils, petrolatum, polyglycerol methyl esters and esters), skin conditioning agents, vitamins and herbal extracts can be added to further improve conditioning performance. Fragrances and dyes may also be added to further enhance the appearance and smell of the finished product. Suitable preservatives, such as benzyl alcohol, methyl paraben, propyl paraben, methylchloroisothiazolinone//methylisothiazolinone, phenoxyethanol, imidazolidinyl urea and DMDM hydantoin, may be utilized.

If necessary, additional thickeners may be added to achieve a desired viscosity for a particular composition. Such thickening agents may include, for example, esterquats, amidoquats, steramidopropyl dimethyl amine quat and polymeric thickeners such as cellulosic polymers, acrylic polymers, and hydroxyl propyl guar gum.

When formulated for personal care, the compositions containing the structured surfactant system typically have a pH of between about 4.0 to about 8.5, alternatively between about 5.0 to about 7.0. Techniques for controlling pH at recommended usage levels include the use of buffers, alkali and acids and are known to those skilled in the art. Optional pH adjusting agents can include, but are not limited to, citric acid, succinic acid, phosphoric acid, sodium hydroxide, sodium carbonate, and the like.

EXAMPLES

The following examples describe some of the preferred embodiments of the present technology without limiting the technology thereto. Other embodiments include, but are not limited to, those described in the above written description, including additional or alternative components, alternative concentrations, and additional or alternative properties and uses. In the following examples, all proportions are based on weight percentages of active ingredients based on the total weight of the composition, unless stated to the contrary.

TABLE A

| Composition Trade Names & Abbreviations | |
|---|---|
| ALPHA-STEP ® PC-48 | sodium methyl 2-sulfolaurate and disodium 2-sulfolaurate |
| STEOL ® CS-270-E | sodium salt of $C_{12}$-$C_{14}$ alkyl ethoxy sulfate with 2 moles ethylene oxide per mole of alcohol |
| STEPANOL ® ALS 25 | Ammonium lauryl sulphate |
| AMMONYX ® LO | Lauramine oxide |
| AMMONYX ® LMDO | Lauramidopropylamine oxide |
| STEPAN-MILD ® GCC | Glyceryl caprylate/caprate |
| PLANTACARE ® 818UP | $C_8$-$C_{16}$ fatty alcohol glucoside |
| NINOL ® 40C0-E | Cocamide diethanolamine |
| NINOL ® COMF-N | Cocamide monoethanolamine |

ALPHA-STEP® PC-48, STEOL® CS-270-E, AMMONYX® LO, AMMONYX® LMDO, NINOL®COMF-N, NINOL® 4000-E, STEPANOL® ALS 25 and STEPAN-MILD® GCC are commercially available from Stepan Co., Northfield, Ill. PLANTACARE® 818UP is commercially available from BASF/Cognis.

Example 1

A series of formulations were prepared by mixing Ammonyx® LO amine oxide, and Stepan-Mild® GCC glyceryl caprylate/caprate in ratios of amine oxide to glyceryl caprylate/caprate ranging from 1:3 to 2:1. Total surfactant for each formulation was 15% by weight. Table B shows the ratio of each surfactant and the visual results for each formulation.

TABLE B

| Ammonyx ® LO Plus Stepan Mild ® GCC w/w Blends in Water 15% Total Surfactant | |
|---|---|
| Amine Oxide:GCC Surfactant Ratio | Result |
| 1:3 | Opaque liquid - about 33% v/v |
| | Clear liquid - about 7% v/v |
| | Clear liquid - about 60% v/v |
| 1:2 | Cloudy liquid - about 10% v/v |
| | Clear liquid - about 90% v/v |
| 1:1.5 | Structured liquid with high degree of clarity that suspends bubbles - 100% |
| 1.25:1 | Structured liquid with high degree of clarity that suspends bubbles - 100% |
| 1.5:1 | Turbid liquid - about 80% v/v |
| | Clear liquid - about 20% v/v |
| 2:1 | Turbid liquid - about 10% v/v |
| | Clear liquid - about 90% v/v |

Structured liquids were obtained over the ratio of 1:1.5 to 1.25:1 amine oxide to glyceryl caprylate/caprate, with clarity increasing with increased amount of amine oxide. The highest degree of clarity was obtained at 1.25:1 w/w amine oxide:glyceryl caprylate/caprate

Example 2

Glycerol was added to blends of 1.25:1 w/w amine oxide:glyceryl caprylate/caprate to determine whether added glycerol could improve the optical clarity of the blends. Table C shows the formulations prepared with added glycerol.

TABLE C

Formulations with Added Glycerol

| Component % w/w | Sample 1(a) | Sample 1(b) | Sample 1(c) |
|---|---|---|---|
| Amine oxide (Ammonyx ® LO) | 8.33 | 8.33 | 8.33 |
| Stepan-Mild ® GCC | 6.66 | 6.66 | 6.66 |
| Glycerol | 1.00 | 5.00 | 10.00 |
| Water | Bal | Bal | Bal |

The formulations were prepared by mixing all the components by hand at room temperature and storing overnight at 55° C., re-stirring, and then cooling to room temperature. All the formulations were structured liquids that suspended air. There was a noticeable difference in clarity between the samples. The sample with 5% glycerol was the clearest, with a very high degree of clarity, followed by the sample with 10% glycerol, then the sample with 1% glycerol. These results show that adjusting the refractive index of the continuous phase can improve the clarity of liquid crystal dispersions.

Example 3

Glyceryl Caprylate/Caprate with Other Surfactants

Formulations were prepared by mixing glyceryl caprylate/caprate with different hydrophilic surfactants and dispersing in water. Glycerol was incorporated as necessary, to adjust the refractive index. The different formulations are shown in Table D.

TABLE D

| Component % w/w | 2 | 3 | 4 | 5 | 6 | 7 |
|---|---|---|---|---|---|---|
| STEPAN-MILD ® GCC | 11.25 | 11.25 | 10.0 | 6.66 | 9.72 | 7.14 |
| Lauramine oxide (ex Ammonyx ® LO) | — | — | — | 8.33 | — | — |
| Sodium methyl 2-sulfolaurate and disodium 2-sulfolaurate (ex ALPHA-STEP ® PC-48) | 3.75 | — | — | — | — | — |
| Sodium laureth (2 EO) sulphate (ex STEOL ® CS-270-E) | — | — | 2.5 | — | 3.95 | — |
| Ammonium Lauryl Sulfate (ex STEPANOL ® ALS 25) | — | 3.75 | — | — | — | — |
| Alkyl polyglucoside (ex Plantacare ® 818UP) | — | — | — | — | — | 7.13 |
| Glycerol | 5.0 | — | 5.0 | 5.0 | 5.0 | 4.76 |
| Water | Balance | Balance | Balance | Balance | Balance | Balance |

Each of the formulations was prepared by mixing the components together by hand at room temperature, storing overnight at 55° C., re-stirring, and then cooling to room temperature. Sample 2, comprising a ratio of about 3:1 w/w GCC:Alpha-Step® PC 48 and total surfactant of about 15% by weight, provides a strong structured surfactant suspending system that is only slightly turbid. Sample 3, comprising a ratio of about 3:1 GCC:ALS and total surfactant of about 15% by weight also provides a strong structured surfactant suspending system that is slightly turbid. Sample 4, comprising a ratio of about 4:1 GCC:SLES and total surfactant of about 12.5% by weight is effectively transparent.

Example 4

Concentrated Blend

The following concentrated blend was prepared based on the Sample 1(b) amine oxide/GCC formulation of Example 2.

| | |
|---|---|
| 25.00 g | Glycerol |
| 33.33 g | Stepan-Mild ® GCC |
| 138.88 g | Ammonyx ® LO |

The resulting blend is a turbid "thin lamellar" phase—very mobile at 50% w/w solids, 38% total surfactant. When 40 g of this blend is gently stirred into 60 g of water at room temperature a transparent structured system is readily formed.

Example 5

Formulations were prepared utilizing the structured surfactant suspending systems to suspend beads in the compositions. The formulations are shown in Table E. The formulations were found to be phase stable and non-sedimenting after storing for 3 Months at room temperature and also at 40° C. and 3° C.

TABLE E

| Component % w/w | Formula 1 | Formula 2 |
|---|---|---|
| Sodium laureth sulfate (2 EO) ex STEOL ® CS-270-E (Stepan) | 2.5 | — |
| STEPAN-MILD ® GCC (Stepan) | 10.0 | 6.66 |
| Amine Oxide ex. Ammonyx ® LMDO (Stepan) | — | 6.66 |
| Ninol ® 40C0-E - coconut diethanolamide (Stepan) | — | 6.66 |
| Glycerol | 5.0 | — |
| Perfume | — | 0.5 |
| Blue Unispheres NT 2103 (Induchem USA) | 0.5 | 0.5 |

TABLE E-continued

| Component % w/w | Formula 1 | Formula 2 |
|---|---|---|
| Preservative Kathon CG (Dow) | 0.02 | 0.02 |
| Viscosity (cps)@ 23 Deg. Centigrade (Brookfield RVT, spindle 5, speed 100) | 2020 | 2086 |
| Appearance | Transparent base with suspended beads | Transparent base with suspended beads |

Formula 1 was prepared by firstly dissolving the sodium laureth sulfate (2 EO) in water; heating to 60° C. with gentle stirring; adding glycerol, then Kathon, then beads, and finally the GCC. Gentle stirring was maintained throughout; agitation was stopped as soon as the sample thickened. Formula 2 was prepared by mixing amine oxide with water and Kathon and heating to 60° C. The remaining ingredients were mixed together at room temperature before adding the hot amine oxide solution to this mix with gentle agitation and stirring until the sample thickened. Before bottling, both Formula 1 and Formula 2 were thermostated at 60° C. for 16 Hrs.

Formula 1 (minus the beads) was found to have a viscosity of ca. 2000 cps at 22° C. when measured on a Brookfield RVT viscometer at 21 reciprocal seconds. Viscosity (at the same temperature) was then measured over the range 0.1 to 100 reciprocal seconds on a Mettler RM260 rheometer. The sample was found to be shear thinning and showed a quick recovery back to the starting viscosity on cessation of shear.

Example 6

A handwash formulation was prepared utilizing the structured surfactant suspending system and mica and glitter was suspended in it. The composition is shown in Table F. It was found to be phase stable and non-sedimenting after storing for 3 Months at room temperature and also at 40° C. and 3° C. It was found to foam well in use and leave the hands feeling soft and moisturized.

TABLE F

| Component % w/w | Composition A with mica | Composition B with glitter |
|---|---|---|
| STEPAN-MILD ® GCC (Stepan) | 5.0 | 5.0 |
| Amine Oxide ex. Ammonyx LMDO ® (Stepan) | 5.0 | 5.0 |
| Ninol 40C0-E ® - coconut diethanolamide (Stepan) | 4.5 | 4.5 |
| Tetraglycerol monooleate | 0.5 | 0.5 |
| Perfume | 0.5 | 0.5 |
| Mica "Bright Gold" Colorona ® (Merck) | 0.05 | |
| Glitter "Silver Flash" 15-150 microns (Sumicos) | | 0.05 |
| Preservative Kathon GC ® (Dow) | 0.02 | 0.02 |
| Viscosity (cps)@ 23 Deg. Centigrade (Brookfield RVT, spindle 5, speed 100) | 1084 | 1032 |
| Appearance | Visually pleasing swirls of gold speckles | Visually pleasing swirls of glitter |

The samples were prepared by mixing amine oxide with water and Kathon and heating to 60° C. The remaining ingredients were mixed together at room temperature before adding the hot amine oxide solution to this mix with gentle agitation and stirring until the sample thickened. Before bottling, the samples were thermostated at 60° C. for 16 Hrs.

Example 7

Bodywash formulations containing suspended oil droplets were prepared. The compositions are shown in table G. They were found to be phase stable with no separation after storing for 3 Months at room temperature and also at 40° C. and 3° C. They foamed surprisingly well in use and delivered oil onto the skin to provide a unique "two in one" cleansing/moisturizing experience.

TABLE G

| Component (% w/w) | Formula 1 | Formula 2 |
|---|---|---|
| STEPAN-MILD ® GCC (Stepan) | 12.85 | 14.33 |
| Glycerol | | 2.0 |
| Paraffinum Liquidum | 20.0 | 2.5 |
| Refined Shea Butter | | 0.2 |
| Perfume Hypo 301 (Givaudan) | | 0.2 |
| ALPHA-STEP ® PC-48 (alpha sulfo methyl ester blend ex Stepan) | | 1.84 |
| Ammonium lauryl sulfate ex STEPANOL ® ALS 25 (Stepan) | 4.81 | 2.75 |
| Citric acid | | 0.044 |
| Trisodium citrate | | 0.224 |
| Preservative Kathon GC (Dow) | 0.02 | 0.02 |
| Viscosity (cps)@ 23 Deg. Centigrade (Brookfield RVT, spindle 5, speed 100) | | 1936 |
| Comments | Demonstration bodywash chassis containing a very high level of oil. Opaque mousse. | Optimized bodywash. Opaque pourable liquid. |

Formula 2 was prepared by mixing together the GCC, paraffinum liquidum, shea butter, and perfume and warming gently (30° C.) until a clear solution was obtained. This mixture was then poured into a stirred solution of the remaining components at room temperature. The sample was stirred efficiently (without entraining air) until it was smooth and homogeneous.

Formula 2 was examined by small angle X-ray, count time 600 seconds, room temperature. The x-ray results show weak scattering with a hump around 45 Angstroms; this is consistent with microvesicles that contain only a few concentric shells.

Formula 2 was analyzed by freeze fracture electron microscopy; the results are consistent with a droplet size less than 2500 Angstroms in diameter. Calculations indicate that spherulites with 5-7 shells and a bilayer separation of 45 Angstrom will have a size of the order of ca. 500 Angstroms. It is difficult to fully resolve structure units around 500 Angstroms using this technique.

Example 8

A glyceryl caprylate/caprate and ammonium lauryl sulphate structured surfactant system was used to prepare two water-based sugar scrub compositions. Typically sugar and salt scrubs are predominantly oil based, and a water-based scrub offers certain advantages. The scrubs are listed in Table H. They were found to be phase stable with no separation after storing for 1 Month at room temperature and also at 45° C. and 0° C.

TABLE H

| Component (% w/w) | Formula A | Formula B |
|---|---|---|
| STEPAN-MILD ® GCC (Stepan) | 6.63 | 4.86 |
| Ammonium lauryl sulfate ex STEPANOL ® ALS 25 (Stepan) | 2.21 | 1.62 |
| Sucrose (granulated white table sugar) | 70.3 | 70.0 |
| Soybean oil | | 4.53 |
| Shea butter | | 0.4 |
| Perfume | 0.4 | 0.4 |
| Citric acid | 0.014 | 0.014 |
| Trisodium citrate | 0.083 | 0.083 |
| water | balance | balance |
| pH | 5.7 | 5.7 |

The scrubs were prepared by charging all the components to the water then stirring gently at room temperature until a smooth homogeneous consistency was obtained.

Example 9

An antidandruff shampoo was formulated (Table J) containing 1% zinc omadine. It was found to be phase stable with no separation after storing for 3 Months at room temperature and also at 45° C. and 0° C.

TABLE J

| Component (% w/w) | |
|---|---|
| STEPAN-MILD ® GCC (Stepan) | 9.50 |
| Ammonium lauryl sulfate ex STEPANOL ® ALS 25 (Stepan) | 3.27 |
| Ninol ® coconut monoethanolamide (Stepan) | 0.55 |
| Sodium laureth sulfate (2 EO) ex STEOL ® CS-270-E (Stepan) | 0.56 |
| Zinc omadine slurry - 48% aqueous dispersion (Arch) | 2.4 |
| Perfume | 0.5 |
| Preservative Kathon CG (Dow) | 0.02 |
| water | balance |
| Product aspect | Dense white opaque liquid |

TABLE J-continued

| Component (% w/w) | |
|---|---|
| Viscosity (cps)@ 23 Deg. Centigrade (Brookfield RVT, spindle 4, speed 100) | 1480 |

The composition was prepared at room temperature with a low shear paddle stirrer by dissolving the Ninol® into the GCC, glyceryl caprylate/caprate then, adding to this the ammonium lauryl sulfate, the sodium laureth sulfate, water, zinc omadine, Kathon, and finally perfume; maintaining gentle shear without entraining an excessive amount of air.

Example 10

Various compounds were found to have a good clarifying effect on the basic glyceryl caprylate/caprate and ammonium lauryl sulphate structured surfactant system. Without clarifying agents the composition is slightly turbid. Microscopic examination (polarizing microscope) indicates that the turbidity is due to large extremely faint spherulites. It is believed that the clarifying agents listed below operate by either refractive index matching, or by reducing spherulite size, or (certainly in the case of polyglycerols) by a combination of both mechanisms.

TABLE K

| Component (% w/w) | A | B | C | D | E | F | G |
|---|---|---|---|---|---|---|---|
| STEPAN-MILD ® GCC (Stepan) | 9 | 9 | 9 | 9.6 | 10.6 | 9.6 | 9.6 |
| Ammonium lauryl sulfate ex STEPANOL ® ALS 25 (Stepan) | 3 | 3 | 3 | 3.85 | 3.85 | 3.85 | 3.85 |
| Glycerol | 10 | | 2 | 6 | 6 | 6 | 6 |
| Triglycerol | | 6 | 2 | | | | |
| Cetyl stearyl alcohol | | | | 0.45 | 0.45 | 0.45 | 0.45 |
| POE (20) sorbitan monooleate | | | | 2.0 | | | |
| POE (20) sorbitan monolaurate | | | | | 1.0 | | |
| C12/14 alcohol + 50 moles EO | | | | | | 0.5 | |
| PEG400 | | | | | | | 0.5 |
| Order of clarity by visual comparison (1 = clearest) | 4 | 1 | 1 | 3 | 2 | 3 | 4 |
| Viscosity (cps)@ 23 Deg. Centigrade (Brookfield RVT, spindle 5, speed 100) | 1480 | 1494 | 1476 | 3904 | 2840 | 2084 | 1936 |

Samples are prepared by blending surfactants and additives together at room temperature to give a fluid lamellar 'paste', then adding water and stirring gently until the structured surfactant system forms. Samples are then thermostated at 45° C. for 16 hours. All the samples have a very high degree of clarity but Formulations B and C in Table K are markedly superior—they are almost crystal clear. A combination of glycerol and triglycerol gives the best performance for at least the additives. Samples of narrow cut polyglycerides (−3, −4, and −6 ex Spiga Nord S.P.A.) were examined in the ALS/GCC/Glycerol system. No significant differences were found between them in clarifying effect.

Example 11

Glyceryl caprylate/caprate (Stepan-Mild® GCC) is an approved excipient for oral pharmaceutical formulations. By combining it with high HLB pharmaceutical excipients, several suspension systems useful for formulating insoluble drug particles can be constructed. The ratios of high HLB excipient to Stepan-Mild® GCC required to construct the suspending systems for a number of excipients were determined experimentally and are listed in Table L.

TABLE L

| Sample | High HLB excipient | Ratio of excipient to Stepan-Mild ® GCC w/w | % Actives |
|---|---|---|---|
| A | Sucrose stearate (HLB 15) | 1:1 | 15.0 |
| B | POE(20) sorbitan monolaurate | 1:1 | 15.0 |
| C | POE(20) sorbitan monooleate | 1:1.25 | 15.0 |
| D | Sodium cholate | 1:9.5 | 15.0 |

Samples are prepared by low-shear mixing all components together at room temperature; thermostating for 16 hours at 45° C. then remixing prior to cooling to room temperature. All of the above examples are slightly turbid liquids with viscosities around 2000 cps @ 21 reciprocal seconds. They are birefringent when the bulk sample is viewed through polarizing filters and will suspend particles of solid, liquid or gas.

Example 12

Lauramine oxide was combined with 2.5 and 3.0 mole linear ethoxylated alcohols to produce systems with good potential for suspending agrochemical actives. The ethoxylated alcohols chosen were C11 plus 3EO and C9-11 plus 2.5EO. Table M lists the ratio of lauramine oxide to alcohol ethoxylate that gives a suspending system.

TABLE M

| Ethoxylated Alcohol | Ratio of lauramine oxide to ethoxylated alcohol (w/w) | % Actives |
|---|---|---|
| C9-11 oxo alcohol (75% linear) plus 2.5 EO (Hydroxyl value 203 mg KOH/g) | 1:1.175 | 15.0 |
| C11 oxo alcohol (75% linear) plus 3 EO (Hydroxyl value 185 mg KOH/g) | 1:2.750 | 15.0 |

Samples are prepared by low-shear mixing all components together at room temperature. They are slightly turbid liquids with viscosities around 2000 cps @ 21 reciprocal seconds and will suspend particles of solid, liquid or gas.

Example 13

A suspending system was prepared for use with an agricultural active to prepare an agricultural composition. A chlorothalonil dispersion was prepared by blending the surfactants shown in Table N together before dispersing them in water (at room temperature) and then gently stirring in the chlorothalonil active until a smooth homogeneous sample was obtained. The composition having the formulation shown in Table N was opaque and pourable. It was stable for 3 months at room temperature and showed no signs of sedimentation and/or phase separation.

TABLE N

| Component | (% w/w) |
|---|---|
| C12/C14 fatty alcohol plus 2 EO | 3.4 |
| Amine Oxide ex. Ammonyx LO ® (Stepan) | 2.5 |
| Chlorothalonil (unmilled tech grade 98.1% ex. Sorn Dynamics) | 40.0 |
| Demineralised water | balance |
| Product aspect | Dense off white opaque liquid |
| Viscosity (cps)@ 23 Deg. Centigrade (Brookfield RVT, spindle 4, speed 100) | 2000 |

The present technology is now described in such full, clear, and concise terms as to enable a person skilled in the art to which it pertains, to practice the same. It is to be understood that the foregoing describes preferred embodiments of the present technology and that modifications may be made therein without departing from the spirit or scope of the present technology as set forth in the claims.

What is claimed is:

1. An aqueous structured surfactant system comprising:
from 5% to about 40% by weight of a mixture of surfactants wherein the mixture of surfactants, comprises:
at least one surfactant having an HLB value of less than 10 selected from glyceryl esters having linear saturated alkyl chains, fatty alcohol ethoxylates having linear saturated alkyl chains, and mixtures thereof; and
at least one surfactant having an HLB value of 10 or greater selected from alkyl amine oxide, alkyl sulfate, alkyl ether sulfate, alpha-sulpho methyl esters, sarcosinates, taurides, propionates, betaines, sulfobetaines, glycinates, sodium cholate, alkyl polyglucoside, fatty acid soaps, ethoxylated sorbitan esters, and sucrose esters, the mixture of surfactants having an overall HLB value in the range of about 11 to about 13;
optionally, from about 1% to 15% by weight of the structured surfactant system of one or more hydroxyl containing compounds having at least two hydroxyl groups;
and water in an amount to balance the structured surfactant system to 100%;
wherein the mixture of surfactants forms multilamellar vesicles with a droplet size of less than 2500 angstroms and a bilayer spacing below 60 angstroms;
wherein the structured surfactant system is free of electrolytes, polymeric thickeners, and carbohydrate structurants; and
wherein the structured surfactant system is transparent in the absence of any suspended matter, and has a yield value that enables the structured surfactant system to suspend solid, liquid, or gas particles throughout the system without sedimentation or creaming.

2. The aqueous structured surfactant system of claim 1, wherein the glyceryl esters are glyceryl caprylate/caprate esters.

3. The aqueous structured surfactant system of claim 1, wherein the one or more hydroxyl containing compounds are present in the structured surfactant system in an amount of about 1% to about 10% by weight.

4. The aqueous structured surfactant system of claim 1, wherein the hydroxyl containing compounds comprise glycerol, a polyglycerol or mixtures thereof.

5. The aqueous structured surfactant system of claim 1, wherein the structured surfactant system further comprises particles of solid, liquid or gas suspended stably within the system.

6. The aqueous structured surfactant system of claim 1, wherein the ratio of the at least one surfactant having an HLB value of less than 10 to the at least one surfactant having an HLB value of 10 or greater present in the system is from about 4:1 to about 1:4.

7. A composition comprising the structured surfactant system of claim 1.

8. The composition of claim 7, wherein the composition is a personal care composition, a pharmaceutical preparation, a laundry composition, a fabric softener composition, an agricultural composition, or a hard surface cleaner.

9. A personal care composition comprising:
(a) a structured surfactant system comprising:
  (i) from about 5% to about 40% by weight of the structured surfactant system of a mixture of surfactants, wherein the mixture of surfactants comprises at least one surfactant having an HLB value of less than 10 selected from glyceryl esters having linear saturated alkyl chains, fatty alcohol ethoxylates having linear saturated alkyl chains and mixtures thereof, and at least one surfactant having an HLB value of 10 or greater selected from alkyl amine oxide, alkyl sulfate, alkyl ether sulfate, alpha-sulpho methyl esters, sarcosinates, taurides, propionates, betaines, sulfobetaines, glycinates sodium cholate, alkyl polyglucoside, fatty acid soaps, ethoxylated sorbitan esters, and sucrose esters, wherein the mixture of surfactants has an overall HLB value in the range of about 11 to about 13,
  (ii) optionally, from about 1% to about 15% by weight of the structured surfactant system of a hydroxyl-containing material having at least two hydroxyl groups, and
  (iii) water in an amount to balance the structured surfactant system to 100%,
  wherein the mixture of surfactants produces multilamellar vesicles with a droplet size of less than 2500 angstroms and a bilayer spacing below 60 angstroms; and
(b) at least one of solid, liquid or gaseous particles suspended in the structured surfactant system.

10. The personal care composition of claim 9, wherein the surfactant having an HLB value of less than 10 is glyceryl caprylate/caprate.

11. The personal care composition of claim 9, wherein the at least one surfactant having an HLB value of 10 or greater comprises alkyl amine oxide, alkyl sulfate, alkyl ether sulfate, alkyl polyglucoside, fatty acid soaps, ethoxylated sorbitan esters, and sucrose esters.

12. The personal care composition of claim 9, wherein the at least one hydroxyl containing compound is present in the structured surfactant system in an amount of about 1% to about 10% by weight.

13. The personal care composition of claim 9, wherein the hydroxyl containing compound comprises glycerol, a polyglycerol or mixtures thereof.

14. The aqueous structured surfactant system of claim 1, wherein the surfactant having an HLB value of less than 10 does not comprise a fatty acid.

15. The aqueous structured surfactant system of claim 1, wherein the glyceryl esters have an alkyl chain length of 6 to 18 carbon atoms.

16. The aqueous structured surfactant system of claim 1, wherein the fatty alcohol ethoxylates have from 1 to 4 moles of ethylene oxide.

* * * * *